United States Patent [19]

Cooper

[11] 3,979,329

[45] Sept. 7, 1976

[54] CARBON MOLECULAR SIEVE CATALYST

[75] Inventor: Barry John Cooper, London, England

[73] Assignee: Johnson Matthey & Co., Limited, London, England

[22] Filed: Feb. 19, 1974

[21] Appl. No.: 443,787

Related U.S. Application Data

[63] Continuation of Ser. No. 97,043, Dec. 10, 1970, Pat. No. 3,793,224.

[30] Foreign Application Priority Data

Dec. 12, 1969  United Kingdom............... 60743/69

[52] U.S. Cl.............................. 252/422; 252/441; 252/447
[51] Int. Cl.²..................... B01J 37/00; B01J 29/02; B01J 21/18; B01J 23/42
[58] Field of Search .......... 252/422, 423, 447, 444, 252/445, 446, 424, 441; 260/683.9; 117/226, 46 CC, 46 CB; 423/449, 445

[56] References Cited
UNITED STATES PATENTS

| 3,446,865 | 5/1969 | Roth et al.............................. 252/447 |
| 3,617,481 | 11/1971 | Voorhies, Jr. ....................... 252/447 |
| 3,793,224 | 2/1974 | Cooper................................ 252/422 |
| 3,793,354 | 2/1974 | Schwager et al..................... 252/447 |

FOREIGN PATENTS OR APPLICATIONS

| 660,296 | 3/1963 | Canada................................ 252/422 |
| 1,138,307 | 1/1969 | United Kingdom................. 252/444 |
| 932,387 | 7/1963 | United Kingdom................. 252/444 |
| 1,147,563 | 4/1969 | United Kingdom................. 252/430 |

OTHER PUBLICATIONS

*Angewanote Chemie* (International Edition in English) vol. 2, 1963; pp. 67–72, "Reactions of Graphite with Metal Chlorides" by W. Rüdorf et al.

*Primary Examiner*—Winston A. Douglas
*Assistant Examiner*—P. E. Konopka
*Attorney, Agent, or Firm*—Cushman, Darby & Cushman

[57] ABSTRACT

A method of preparing a selective catalyst which includes the steps of polymerizing furfuryl alcohol in an acidic solution of a platinum salt, curing the polymer and carbonizing the same, the curing and carbonizing being carried out in an inert atmosphere.

2 Claims, No Drawings

CARBON MOLECULAR SIEVE CATALYST

This is a continuation of application Ser. No. 97,043, filed Dec. 10, 1970, now U.S. Pat. No. 3,793,224.

This invention relates to catalysts and, more particularly, to catalysts which are selective or resistant to poisoning or both.

By "catalysts which are selective" is meant catalysts having the property, in the presence of substances between which certain reactions may be catalysed, of catalysing one or more of the reactions in preference to, or to the exclusion of, the others. Throughout this specification, this property will be referred to as "selectivity" and catalysts having this property will be described as "selective catalysts".

One way in which a selective catalyst may be prepared is to deposit catalytically active material within the pores of a support material having molecular sieve properties so as to form catalytically active sites within the pores. By molecular sieve properties of a support material is meant that the pores of the support are sufficiently small to prevent molecules above a certain size from entering them. The pores thus deny access to the active sites within the pores of certain sized molecules but permit molecules which are smaller than the pore size to reach the sites. The physical structure of the support material thus dictates which molecules in a given reaction system may reach the catalytically active sites within the material and therefore, which molecules may be available to take part in chemical reactions at these sites. The physical structure of the support material thus confers selectivity on the catalyst. Similarly, the physical structure of the support may protect the catalyst material within the pores from contact with large poison molecules which, if they could enter the pores, could reduce the activity of the catalyst to zero.

It is an object of this invention to provide a molecular sieve embodying a selective catalyst which may be readily prepared from commonly occurring materials, which is cheap to produce and which allows of several alternate methods of production.

It has been determined that molecular sieve carbon, (that is, carbon having molecular sieve properties) made, for example, by carbonising organic material is eminently suitable for the preparation of selective catalysts.

According to a first feature of the present invention, a selective catalyst, as heretobefore defined, comprises a catalytically active material associated with molecular sieve carbon in such a manner that the said carbon will prevent access to the catalytically active material of molecules having a size above a predetermined value.

According to further separate features of the invention:

a. the molecular sieve carbon may be:
  i. substantially amorphous;
  ii. prepared by carbonising organic materials and, preferably, polymerised organic materials;
b. the catalytically active material may be:
  i. deposited within the pores of the molecular sieve carbon;
  ii. coated with a layer of molecular sieve carbon;
  iii. deposited on a support, preferably a large area support, and the resulting supported catalyst coated with a layer of molecular sieve carbon.

A further feature of the invention includes a method of preparing a selective catalyst which comprises forming a dispersion of a catalytically active material in an aliphatic alcohol, polymerising said alcohol to form a thermosetting polymeric resin and carbonising said resin in an inert atmosphere.

The invention also includes a method of preparing a selective catalyst comprising depositing a catalytically active material on a support, polymerising an alcohol to form a liquid polymer resin, coating the supported catalytically active material with a layer of said liquid resin and curing and carbonising the resin coating in an inert atmosphere.

Preferably the catalytically active material consists of platinum and the dispersion of the catalytically active material may comprise an acidic solution of a salt of a desired catalytically active metal.

Certain methods are described in the following examples.

EXAMPLE 1

In this example, a method is described which has been used for preparing a selective catalyst in which the catalytically active material is deposited within the pores of amorphous molecular sieve carbon.

In general, the method comprises forming a dispersion of platinum in an aliphatic alcohol medium in the manner described in out British Patent No. 1,147,563; polymerising the alcohol and then curing and carbonising the resultant polymeric resin in an inert atmosphere.

In more detail, the method was as follows:

1.2g of platinum oxide was weighed into a vessel, and the vessel flushed with nitrogen for 15 min. 30 ml. of furfuryl alcohol and 7 ml. of formaldehyde solution were added under a stream of nitrogen and the mixture stirred and warmed to 40°C. A further 5 ml. of formaldehyde solution were added, and the mixture left for ½ hour during which time the platinum oxide was completely reduced to colloidal platinum. At this stage another 5 ml. of formaldehyde solution were added and the suspension heated to 90°C for ½ hour, following which 0.15 ml. of orthophosphoric acid solution (1 vol. $H_3PO_4$ to 2 vol. $H_2O$) were added. The suspension was kept at 90°C. for another hour, during which time partial polymerisation to a viscous liquid occured. The polymer was cured at 110°C. for 16 hours and at 200°C. for 6 hours under nitrogen. After crushing to form particles which would pass through a 2 mm mesh, the particles were carbonised at 640°C. for 4 hours under oxygen-free nitrogen.

The resulting catalyst contained 5.72% by weight of platinum. However, by varying the quantity of platinum oxide used to produce the dispersion the concentration of platinum may be varied at will, though practical limits in the catalyst would probably be in the range 0.1% – 20% platinum by weight. Further, the same method may also be used for the preparation of selective catalysts containing alloys of platinum and rhodium, containing up to 50% rhodium.

EXAMPLE 2

In this example, a method is described for the preparation of a selective catalyst comprising a supported catalyst coated with a layer of molecular sieve carbon.

In general, the method comprises forming a liquid polymer resin by polymerising an alcohol; covering the supported catalyst with the liquid resin; allowing excess resin to drain away and, thereafter, curing and carbonising the resin coating.

In more detail, the method used was as follows:

A reactor was flushed for 15 mins. under nitrogen and a solution containing 30 ml. furfuryl alcohol and 7 ml. formaldehyde (40% HCHO in water) added and warmed to 40°C. 5 ml. of formaldehyde solution was then added and the solution stirred for ½ hour when a further 5 ml. of formaldehyde solution were added and the whole heated to 90°C. for 1½ hours. Next, 0.15 ml. of orthophosphoric acid solution (1 vol. $H_3PO_4$ to 2 vol. $H_2O$) was added and heating continued at 90°C. for 1 hour. The hot liquid polymer was then poured over granules of a 2% Pt on charcoal catalyst which were then allowed to drain at 90°. for 1 hours. The resin coating was then cured and the catalyst carbonised as described in Example 1.

The catalysts prepared in Examples 1 and 2 were found to be highly selective in hydrogenation reactions. Samples of the catalysts, for example, selectively hydrogenated linear olefinic molecules in a mixture of linear and branched chain olefins. The catalysts are also resistant to poisoning by large poison molecules such as molecules of sulphur compounds.

The results of these tests on the catalysts are summarised in Table 1.

A further method of preparing carbon molecular sieve catalysts is to utilize an acidic solution of a salt of the desired catalytically active metal.

EXAMPLE 3

5 ml. of an aqueous solution of chloroplatinic acid (200g/1 Pt) were added to 20 ml. of furfuryl alcohol and polymerisation induced by slight warming. After the vigorous polymerisation had ceased the solid polymer was removed from the reaction flask and dried by heating at 110°C under nitrogen. The polymer was then cured at 200°C for 16 hr. and carbonised at 650°C for 4 hr., both under nitrogen.

Similar catalysts were prepared containing Fe, Co, Ni, Cu, Ru, Rh, Pd, Os and Ir as the catalytic metal by adding aqueous solutions of the chlorides acidified with hydrochloric acid to furfuryl alcohol and then treating in the same manner as for the platinum catalyst.

A further method of preparation that may be used is the deposition of active materials from the gas phase. For example volatile salts such as anhydrous ferric chloride, aluminum chloride, copper chloride ($CuCl_2$) and tungsten chloride ($WCl_6$) may be sublimed on to the carbon.

EXAMPLE 4

TABLE 1

THE HYDROGENATION OF LINEAR AND OF BRANCHED OLEFINS OVER CONVENTIONAL PLATINUM/CHARCOAL AND OVER PLATINUM/CARBON MOLECULAR SIEVES

| A | $1.78 \times 10^{-4}$ moles/pulse at 25°C. Reciprocal space velocity $9.0 \times 10^{-3}$ g.min/cm³ | | B | $2.00 \times 10^{-4}$ moles/pulse at 30°C. Reciprocal space velocity $4.0 \times 10^{-4}$ g.min/cm³ | |
|---|---|---|---|---|---|
| | Alkane produced ($mole \times 10^4$) | | | Alkane produced ($mole \times 10^4$) | |
| Olefin | Pt/CMS1 | 10% Pt/C | Olefin | Pt/CMS2 | 2%Pt/C |
| a propylene | 0.165 | 1.49 | b butene-1 | 0.22 | 1.77 |
| b butene-1 | 0.06 | 1.28 | c isobutene | 0.02 | 1.14 |
| c isobutene | 0 | 1.32 | e 3,3-dimethyl butene-1 | 0.02 | 0.99 |
| d 3-methyl-butene-1 | 0 | 1.25 | | | |
| Selectivity $\frac{a}{a+c}$ | 1.0 | 0.53 | Selectivity $\frac{b}{b+c}$ | 0.92 | 0.61 |
| Selectivity $\frac{b}{b+d}$ | 1.0 | 0.51 | Selectivity $\frac{b}{b+e}$ | 0.92 | 0.64 | a propylene;        b butene-1;        c isobutene;

C—C=C        C—C—C=C        

d 3-methylbutene-1;        e 3,3-dimethylbutene-1

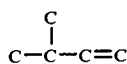        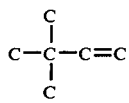

Other methods of preparation, such as adsorption of compounds containing catalytically active species from solution on to previously prepared molecular sieve carbon may also be employed. For example, such compounds as chloroplatinic acid, sodium chloropalladite, rhodium trichloride, ruthenium trichloride, may be adsorbed from an aqueous solution of any other solvent medium in which the salt is sufficiently soluble.

Ferric chloride was successfully incorporated into a composite carbon molecular sieve (CCMS) by the following procedure.

The CCMS was first prepared by a method modified by coating an activated charcoal rather than a platinum/charcoal catalyst as in Example 2. The process of ferric chloride impregnation was as follows:

The CCMS and ferric chloride were placed in two zones of a tubular reactor heated by separate furnaces. The CCMS was then evacuated for 16 hr. to a pressure less than $10^{-4}$ torr at temperatures between 250° and 400°C. The CCMS was cooled to room temperature and chlorine gas admitted to the reactor when the ferric chloride was heated to 250°–400°C causing sublimation of the salt on to the cold CCMS. After heating the CCMS at 250°–400°C for up to 24 hr. the reactor was cooled, excess chlorine pumped off, and the catalyst removed.

Apart from the carbon molecular sieves being selective due to the relative size of the molecules it is believed that they are to some degree "shape selective". There is evidence that with the carbon molecular sieves the pores are shaped somewhat similar to letter boxes and as a result the said sieves exhibit a form of selectivity which it may not be possible to achieve with other molecular sieves. For example, with a carbon molecular sieve it is possible to select between branched aliphatic molecules and aromatic molecules which latter have a flat planar shape and thus more readily enter the "letter box" pore than would branched aliphatic molecules.

I claim:

1. A method of preparing a selective catalyst which includes the steps of treating furfuryl alcohol with an aqueous solution of chloroplatinic acid, warming the mixture to initiate polymerisation of the alcohol, drying the polymer by heating under nitrogen, curing the polymer by heating to 200°C for 16 hours and carbonising the polymer by heating to 650°C for four hours, both the curing and carbonising steps being carried out under nitrogen.

2. A method of preparing a selective catalyst which includes the steps of heating furfuryl alcohol in an aqueous solution of chloroplatinic acid to polymerise said furfuryl alcohol, curing the polymer and carbonising the same, the curing and carbonising being carried out in an inert atmosphere.

* * * * *

UNITED STATES PATENT OFFICE
CERTIFICATE OF CORRECTION

Patent No. 3,979,329     Dated September 7, 1976

Inventor(s) Barry John Cooper

It is certified that error appears in the above-identified patent and that said Letters Patent are hereby corrected as shown below:

The term of this patent subsequent to

February 19, 1991, has been disclaimed.

Signed and Sealed this

Nineteenth Day of April 1977

[SEAL]

Attest:

RUTH C. MASON
*Attesting Officer*

C. MARSHALL DANN
*Commissioner of Patents and Trademarks*